United States Patent [19]

Kim

[11] Patent Number: 4,631,054

[45] Date of Patent: Dec. 23, 1986

[54] APPARATUS AND PROCESS FOR NASO-INTESTINAL INTUBATION

[76] Inventor: Il G. Kim, N. Main St., Hughesville, Pa. 17737

[21] Appl. No.: 672,361

[22] Filed: Nov. 16, 1984

[51] Int. Cl.[4] .............................................. A61M 25/00

[52] U.S. Cl. ...................................... 604/54; 128/772; 604/270; 604/280

[58] Field of Search ........................ 604/54, 96, 97, 98, 604/270, 280, 51, 52, 53; 128/658, 772

[56] References Cited

U.S. PATENT DOCUMENTS

| | | | |
|---|---|---|---|
| 3,043,309 | 7/1962 | McCarthy | 604/54 |
| 3,189,031 | 6/1965 | Andersen | 604/270 |
| 3,394,705 | 7/1968 | Abramson | 604/96 X |
| 4,182,342 | 1/1980 | Smith | 604/270 X |
| 4,270,542 | 6/1981 | Plumley | 604/270 X |
| 4,516,970 | 5/1985 | Kaufman | 604/270 |

*Primary Examiner*—Anton O. Oechsle

*Attorney, Agent, or Firm*—Anthony J. Dixon

[57] ABSTRACT

An endoscopically guided novel naso-intestinal tube for intubation of the duodenum comprising a hollow flexible member, circumferentially mounted mercury bag and a series of drainage ports which is used in a novel intubation process to result in intubation of the duodenum without need of radiation and with minimal patient discomfort.

10 Claims, 5 Drawing Figures

APPARATUS AND PROCESS FOR NASO-INTESTINAL INTUBATION

BACKGROUND OF THE INVENTION

1. Field of the Invention

The present invention relates to intubation of the duodenum and small bowel.

More particularly, it relates to intubation of the long naso-intestinal tube into the duodenum and small bowel to a predetermined and desired location and to a novel long naso-intestinal tube for use therein.

More particularly, the present invention relates to use of an endoscopically guided long naso-intestinal tube which, by the inventive process disclosed herein, is guided to the proper location in the duodemum, and subsequently into the small bowel.

2. The Prior Art

Intubation of the long naso-intestinal tube has long been a problem faced by those skilled in the art.

Rubber or poly vinyl tubes of the type used by Miller and Abbott (Am. J. Sc., 1934, 187:595) and Cantor, (Am. J. Surg. 1947, 73:690) have long been used for this purpose. The success rate for placing these tubes in the proper location has been low and also difficult in regard to conventional methods.

More recent advances include blind approach fluoroscopic placement of naso-intestinal decompression tubes. An example is discussed by F. C. Shipps and C. B. Sayler (*Radiology,* 132:226–227, July, 1979). Still, the failure rate is high by most radiologists due to the difficulty of the process. A need exists for an improved method and apparatus to pass the long tube into the duodenum through the pylorus of the stomach of the seriously ill patient.

U.S. Pat. No. 4,175,564, issued to Kwak illustrates a nasal gastric tube insertion guide and method, however location determination is not satisfactorily shown.

U.S. Pat. No. 3,776,222 issued to Smiddy discloses an intubation for an endotracheal tube using a fiber optic bundle, however, placement of a tube for evacuation is not disclosed nor is location of the tube into the duodenum.

The need therefore still exists to intubate the long naso-intestinal tube through the pylorus of the stomach for intestinal obstructions via easy placement through direct view of flexible gastroduodenoscopic guidance.

This need and others are met by the present invention.

SUMMARY OF THE INVENTION

It is therefore an object of the present invention to provide an endoscopically guided long naso-intestinal tube for intubation of the duodenum and small bowel.

It is a further object to provide such an apparatus as can be predicticably inserted in patients in a predictable manner to a predetermined location.

It is a further object of the invention to provide a process whereby the naso-intestinal tube of the present invention is introduced into the duodenum of the patient.

These and other objects and advantages are achieved by the present invention which comprises an endoscopic guided long naso-intestinal tube comprising:

a. a tubular member having two ends;

b. a rubber mercury bag circumferentially mounted adjacent to one end of the tube;

c. means for connecting the tube to other instruments mounted on the second end of the tube;

d. a series of drainage ports communicating between the inside and outside of the tubes and located along the length of the tube;

e. means for injecting mercury into said bag.

Wherein said tube has an inner diameter large enough to slide over a pre inserted guide wire which can be slidingly removed leaving the tube in place.

The method of the present invention comprises:

a. anesthetism of the patient's throat and nostrils;

b. intubation of a flexible gastroduodenoscope having a biopsy port into the second portion of the duodenum;

c. introduction of a flexible guide wire of at least about twelve feet in length through said biopsy port into the second portion of the duodenum;

d. removal of the flexible gastro duodenoscope;

e. marking of the wire position on the wire;

f. insertion of a lubricated tube through the nostril and into the oral cavity;

g. withdrawal of one end of said tube through the mouth;

h. sliding the guide wire through said tube until it exits the nasal cavity end;

i. removal of the lubricated tube;

j. introduction of the naso-intestinal tube of the present invention over the guide wire in a sliding fashion until the tip is at the desired level as shown by reference to the mark made in "e" above;

k. removal of the guide wire thereby completing the intubation predictably, successfully and without injury to the nasal mucosa or the oral cavity.

The above is accomplished without radiation as is required in the blind fluoroscopic approach.

The present invention will be more clearly understood with reference to the drawings and description of the preferred embodiment which follows.

THE PREFERRED EMBODIMENT

Figure 1:
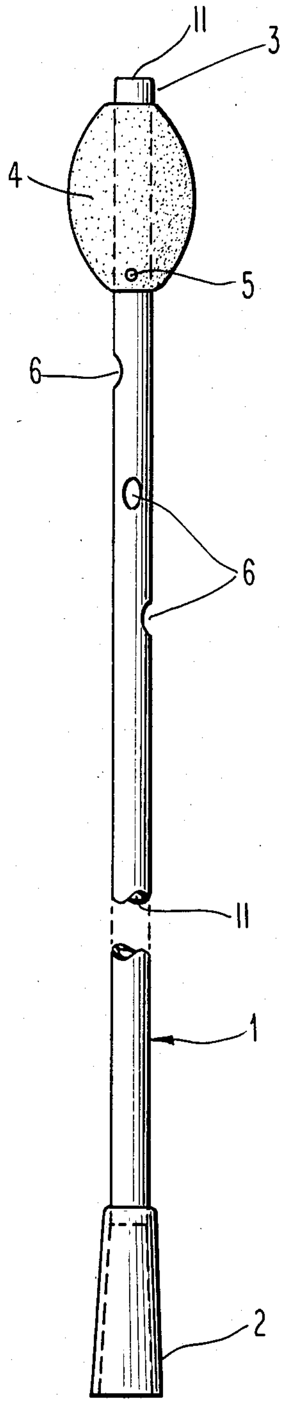
FIG. 1 is a fragmented view of the naso-intestinal tube.
Figure 2:
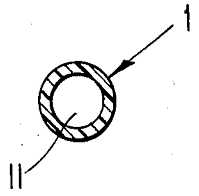
FIG. 2 is a cross sectional view of the tube.

With particular attention to the drawings, the method and apparatus of the present invention will be described.

Referring to FIG. 1, the long naso-intestinal tube, 1, can be seen. The tube has an inner circumference 11, which is large enough to accommodate the guide wire 12, to be discussed later. Note that the tube is provided with connector 2, to attach to other apparatus. Ports 6, are provided for drainage.

The inflatable mercury bag 4, is mounted around tube 1, near the inserted end 3. The extension of a small portion of tube 1, beyond bag 4, allows for ease of insertion without the bag being in the way. It is filled by injection through port 5, which communicates with the interior diameter 4.

The length of the tube contemplated is about seven feet or at least about 245 centimeters. The bag 4, is located about 2 millimeters from end 3 and is about 30 millimeters in length. The ports 6, are spaced over the next 45 millimeters from the end of the bag. The overall diameter is approximately 8.52 millimeters (19 gauge) and an interior diamter of about 6.3 millimeters.

Clear poly vinyl is the preferred material of construction but other sterilizable flexible materials can be utilized without departing from the scope of the present invention.

Figure 3:
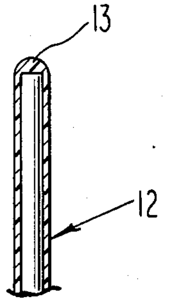
FIG. 3 is a cross sectional view of the guide wire tip.
Figure 5:
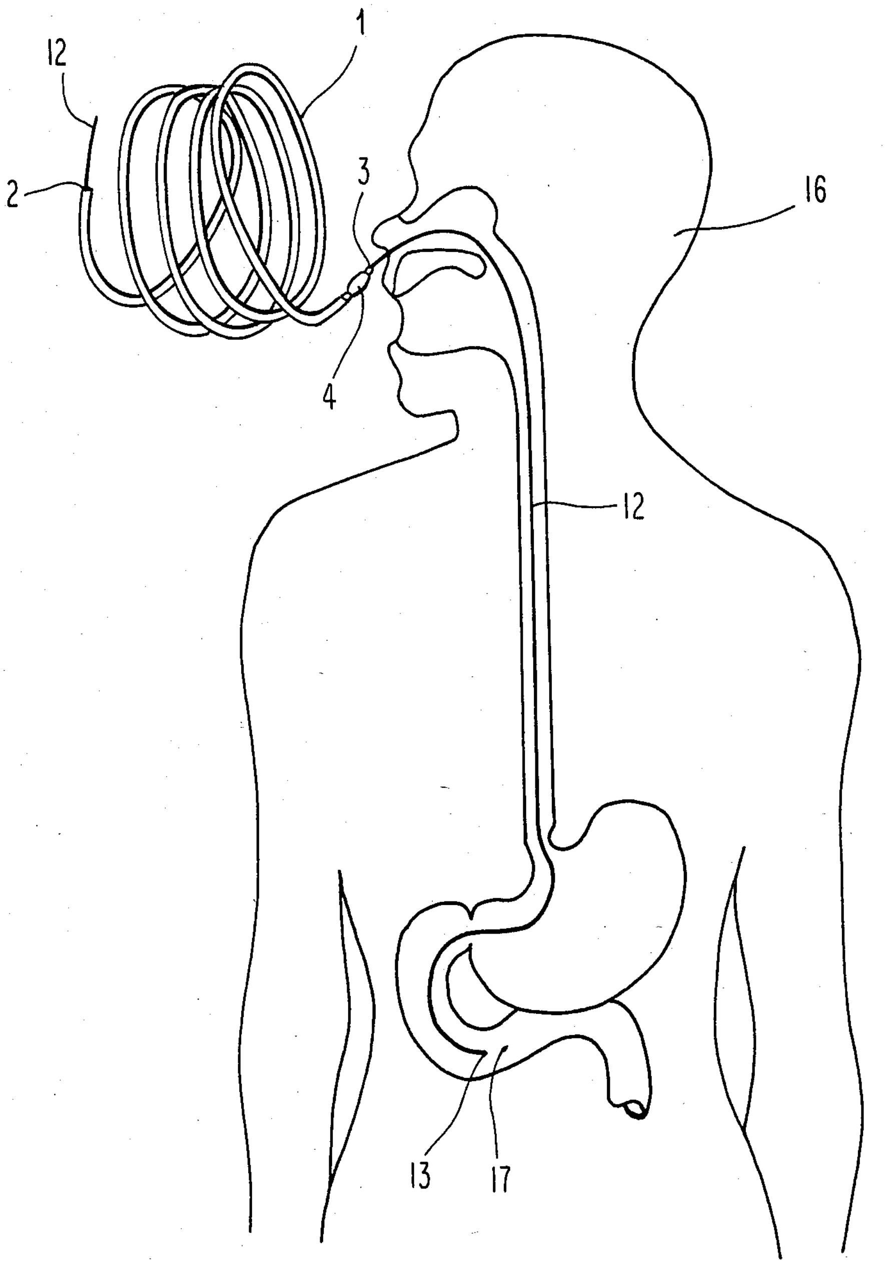
FIG. 5 shows the process of the invention of the tube introduction stage.

FIG. 5 depicts the wire 12 inserted into the patient, 16. The wire tip is bulbous in nature as seen in FIG. 3 and is accommodatingly smaller in diameter than the interior diameter of tube 1. In FIG. 5 sliding insertion of tube 1, is underway over wire 12, and will proceed until tip 3, is located at wire tip 13, in the duodenum, 17.

Figure 4:
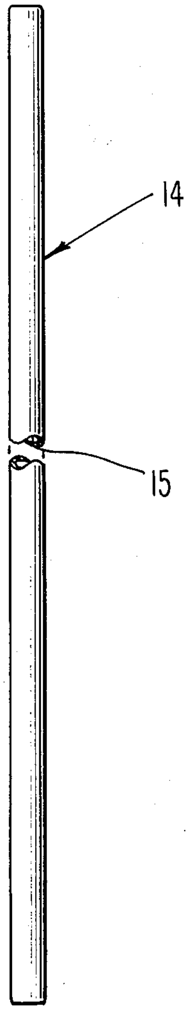
FIG. 4 is a fragmented view of the naso-oral catheter.

The naso-oral catheter used is approximately 550 mm in length (see FIG. 4) with an interior diameter of about 6 mm (18 gauge). Here, as above, clear poly vinyl is preferred.

The process of the invention, utilizing the novel long tube 1 disclosed herein, proceeds as follows:

A flexible gastroduodenoscope, not shown, is intubated into the second portion of the duodenum after Cedacaine spray anesthesia or the like is applied to the patient's throat and nostrils. A well-lubricated, long, flexible guide wire, 12, of about twelve feet in length with a slightly bulbous distal end, 13 which features a flexible safety tip, is introduced into the second portion of the duodenum by direct vision through the biopsy port of the endoscope. The endoscope is slowly withdrawn after viewing the wire location while feeding the guide wire into the scope. As soon as the tip of the endoscope is out of the patient's oral cavity, the guide wire 12, is stabilized and a premarked duodenal level is marked thereon. The level indicates the location of the guide wire tip, FIG. 5.

A well-lubricated, (both inside and out), poly vinyl tube or catheter, 14 is introduced through the nostril, and the tip is withdrawn through the mouth by a long carry-clamp. The end of the guide wire 12, is fed into the catheter 14. The remaining guide wire can then be withdrawn through the nasal cavity via the catheter without injury to the nasal mucosa. The catheter, 14 is then completely withdrawn from the guide wire 12. The guide wire 12, will, of course, remain in place, extending from the nose down to the second portion of the duodenum (FIG. 5).

A well-lubricated, (both inside and out), specially made naso-intestinal poly vinyl, sleeve-type tube of about seven feet in length, 1 with a mercury bag 4, on the side of the tip, is inserted over the endoscopic preguided wire 12. The naso-intestinal tube, 1 is then pushed down over the guide wire until the premarked level of the second portion of the duodenum is reached. The guide wire 12, is then completely withdrawn with only the naso-intestinal tube remaining.

As a result of this process, the naso-intestional tube of the present invention is correctly in place with minimal discomfort or risk to the patient. Further procedures utilizing the tube now in place, may follow.

Although certain sizes are set forth herein, it is solely for the purpose of illustration of a particular embodiment of the invention. Naturally, certain modifications and adjustments may be made without departing from the scope of the present invention.

I claim as my invention:

1. An edoscopic guided naso-intestinal tube in combination with a guide wire comprising a. a tubular member having two ends and b. a diameter accommodatingly larger than said guide wire;

b. a mercury bas circumferentially mounted adjacent to the first end of said tubular member;

c. means for connecting the tubular member to other instruments, said means mounted on the second end of the tubular member;

d. a series of drainage ports defined in the wall of said tubular member to provide communication between the inside and outside of said tubular member located along the length of said tubular member; and e. means for injecting mercury into said mercury bag.

2. The apparatus of claim 1 wherein said tube is at least about two hundred forty-five (245) centimeters.

3. The apparatus of claim 2 wherein said bag is located at about two millimeters from said first end and is about thirty (30) millimeters in length.

4. The apparatus of claim 3 wherein said ports are at least three (3) in number and are of circular cross-section.

5. The apparatus of claim 4 wherein said tube is constructed of transparent poly-vinyl material.

6. A method for intubation of the duodenum of a human patient comprising a. anesthetism of the patient's throat and nostrils;

b. intubation through the oral cavity of a flexible gastro duodenoscope, comprising a biopsy port, Into the second portion of the duodenum;

c. introduction of a flexible guide wire of at least about twelve (12) feet in length through said biopsy port into the second portion of the duodenum to a given position;

d. removal of said duodenoscope;

e. marking of the wire position on said wire;

f. insertion of a lubricated tube through the nostril into the oral cavity;

g. withdrawal of one end of said tube through the mouth;

h. sliding the guide wire through said tube until it exits the nasal cavity end;

i. removal of said tube;

j. introduction of a naso-intestinal tube over said guide wire in a sliding fashion until the desired level is reached wherein said naso-intestinal tube comprises (1) a tubular member having two ends and a diameter accommodatingly larger than a guide wire (2) a mercury bag circumferentially mounted adjacent to the first end of said tubular member (3) means for connecting the tubular member to other instruments said means mounted on the second end of the tubular member (4) a series of drainage ports defined in the wall of said tubular member to provide communication between the inside and outside of said tubular member located along the length of said tubular member; and k. removal of the guide wire thereby completing the intubation.

7. The process of claim 6 wherein said tube is at least about two hundred forty-five (245) centimeters.

8. The process of claim 7 wherein said bag is located at about two (2) millimeters from said first end and is about thirty (30) millimeters in length.

9. The process of claim 8 wherein said ports are at least three (3) in number and are of circular cross-section.

10. The process of claim 9 wherein said tube is contructed of transparent poly-vinyl material.

* * * * *